United States Patent [19]

Clow

[11] Patent Number: 4,715,998

[45] Date of Patent: Dec. 29, 1987

[54] INHALATION APPARATUS

[75] Inventor: Dereck Clow, Keighley, England

[73] Assignee: The BOC Group plc, Windlesham, England

[21] Appl. No.: 845,917

[22] Filed: Mar. 31, 1986

[30] Foreign Application Priority Data

Apr. 4, 1985 [GB] United Kingdom ............... 8508920

[51] Int. Cl.$^4$ .................. B01F 3/04; A61M 15/00
[52] U.S. Cl. ................... 261/142; 128/203.17;
128/203.27; 128/204.13; 219/274; 219/275;
261/104
[58] Field of Search ............... 261/142, 104;
128/203.17, 203.27, 204.13; 219/274, 275

[56] References Cited

U.S. PATENT DOCUMENTS

| | | | |
|---|---|---|---|
| 2,377,527 | 6/1945 | Siefken | 261/104 |
| 2,819,887 | 1/1958 | Eversole et al. | 261/94 |
| 2,955,064 | 10/1960 | Frohmader | 261/94 |
| 3,033,193 | 5/1962 | Rathman | 261/94 |
| 3,045,450 | 7/1962 | Chandler | 261/104 |
| 3,105,860 | 10/1963 | Dunn | 261/104 |
| 3,621,834 | 11/1971 | Keuls | 261/107 |
| 3,861,894 | 1/1975 | Marsh | 55/357 |
| 3,954,920 | 5/1976 | Heath | 128/203.27 |
| 4,201,737 | 5/1980 | Carden | 219/275 |
| 4,430,994 | 2/1984 | Clawson et al. | 128/204.13 |

FOREIGN PATENT DOCUMENTS 1301582 12/1972 United Kingdom .

Primary Examiner—Tim Miles
Attorney, Agent, or Firm—Roger M. Rathbun; Larry R. Cassett

[57] ABSTRACT

A humidifying module 4 is releasably attachable to a heater unit 2 to form an apparatus for delivering humidified gas to a patient and includes a substantially flat wick 6 which absorbs water without any substantial change in its surface area. The wick is contained within a chamber defined by a substantially flat back plate 10 and a front plate 12 including an inlet 20 for gas to be humidified and an outlet 22 for humidified gas.

2 Claims, 5 Drawing Figures

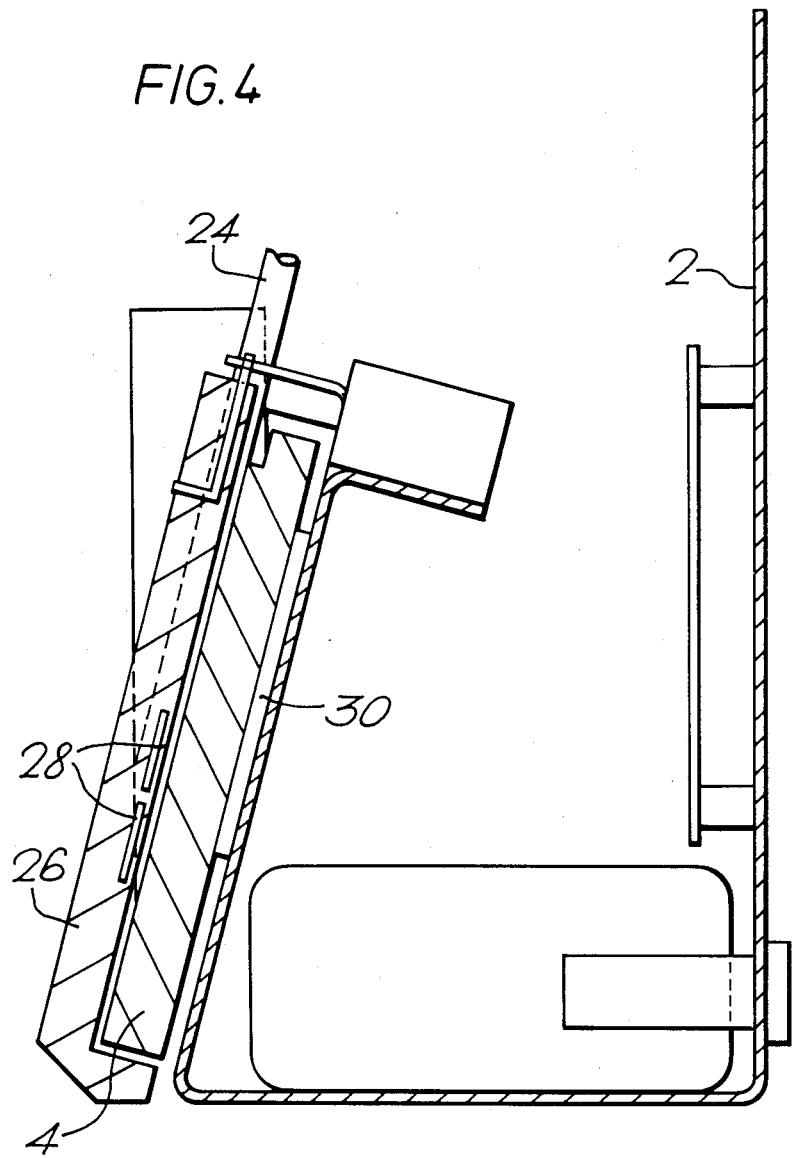

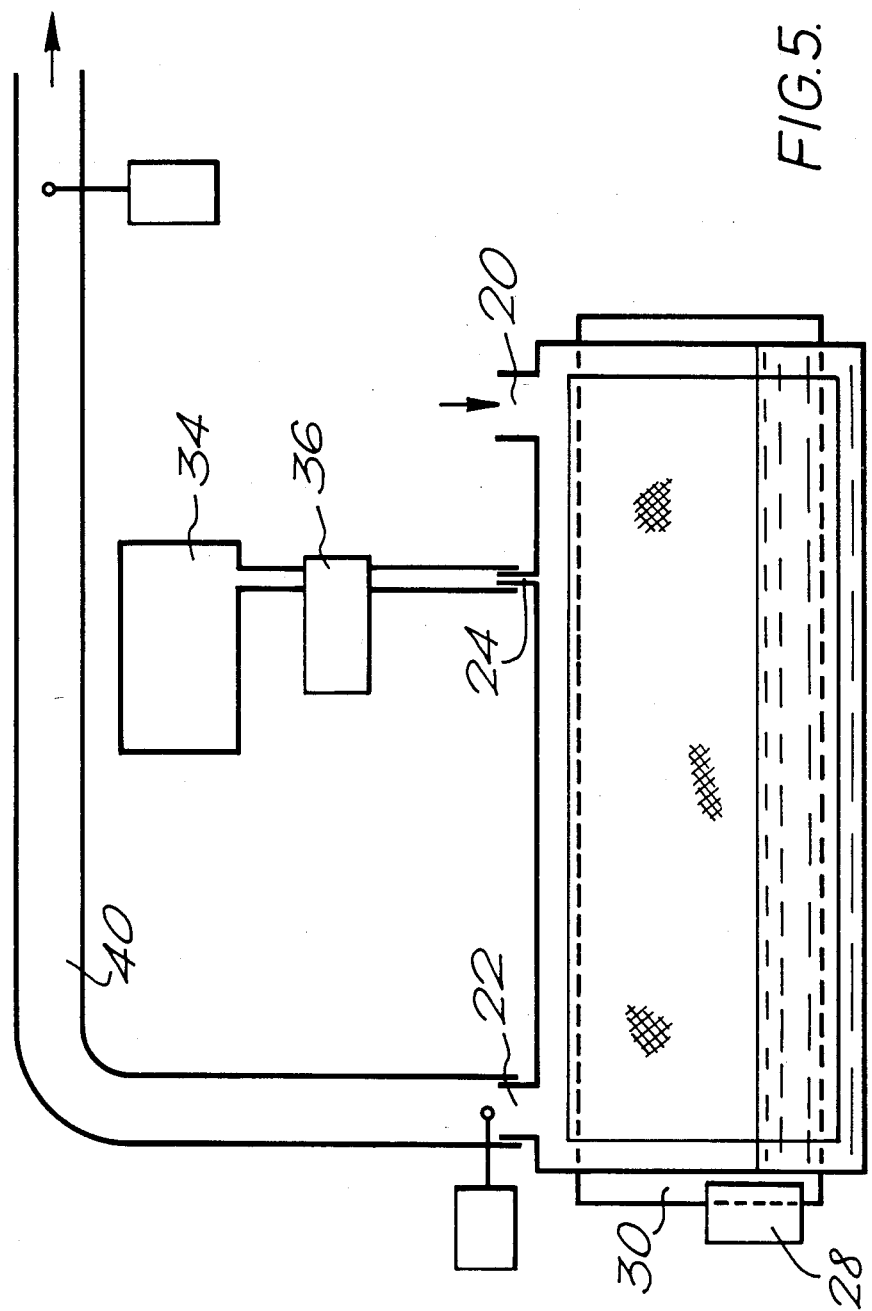

1

INHALATION APPARATUS

BACKGROUND OF THE INVENTION

The present invention relates to inhalation apparatus and in particular to medical humidifiers.

Medical humidifiers are used with intensive care ventilators to heat and humidify dry medical gases to specified levels before said gases are inhaled by a patient.

An example of a known medical humidifier is described in UK patent No. 1301582 which includes a delivery module, a humidifying module and a heater module. The humidifying module consists essentially of a reservoir for water, the base of which is in thermal contact with a heater. The reservoir is enclosed by a cover which also accommodates a scroll covered by a wick material which dips into the water contained within the reservoir.

The humidifying module can be readily removed from the heater module for sterilisation, change of wick or other servicing requirement.

To allow for expansion of the wick, that is, an enlargement of its surface area when it has absorbed water, the wick is formed as a scroll or cylinder. This has the effect of giving the humidifying module a relatively high volume and as a consequence modules of different volume should be used for different types of patient, for example, infants and adults.

SUMMARY OF THE INVENTION

It is an aim of the present invention to provide a humidifying module which is readily detachable from a heating unit and has a small volume and hence a low compliance allowing it to be used in a medical humidifier for many different types of patient.

According to one aspect of the present invention, a humidifying module which is releasably attachable to a heater unit and when so attached forms part of an apparatus for delivering humidified gas to a patient, comprises a substantially flat wick accommodated within a humidifying chamber, the chamber having an inlet for dry gas and an outlet spaced from the inlet for the passage therethrough of the humidified gas.

According to a further aspect of the present invention an apparatus for delivering humidified gas to a patient comprises a humidifying module releasably attached to a heater unit, the module including a substantially flat wick, accommodated within a humidifying chamber, the chamber having an inlet for dry gas and an outlet spaced from the inlet for the passage therethrough of the humidified gas.

BRIEF DESCRIPTION OF DRAWINGS

An embodiment of the invention will now be described by way of example, reference being made to the Figures of the accompanying diagrammatic drawings in which:

FIG. 4 is a part side sectional view of the humidifying module attached to the heater unit; and FIG. 5 is a schematic view of the apparatus of FIG. 1.

DESCRIPTION OF PREFERRED EMBODIMENT

Figure 1:
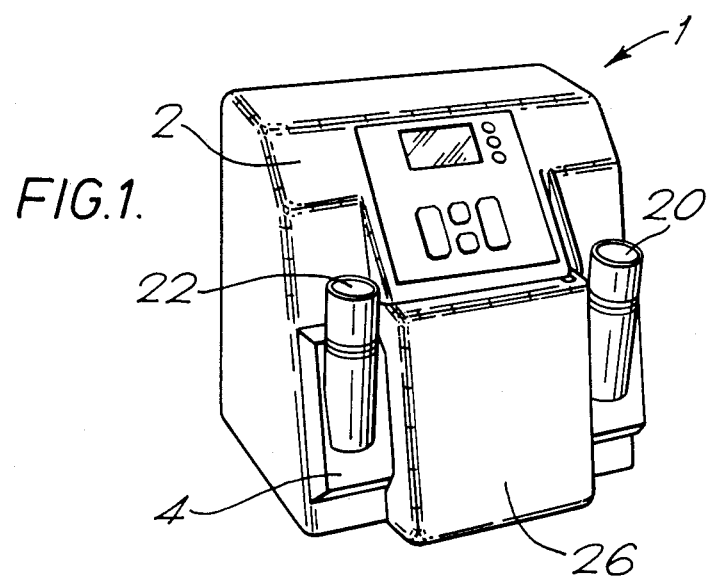
FIG. 1 is a front perspective view of an apparatus for delivering humidified gas to a patient.
Figure 2:
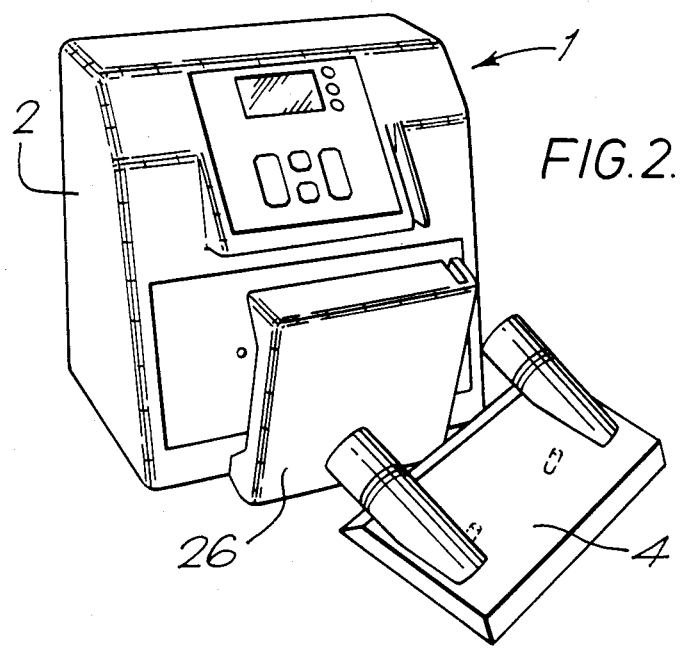
FIG. 2 is a front perspective view similar to FIG. 1, but showing a humidifying module detached from a heater unit forming part of the apparatus of FIG. 1.

As shown in FIGS. 1 and 2, an apparatus 1 for delivering a humidified gas to a patient comprises a heater unit 2, to which is releasably attached a humidifying module 4.

Figure 3:
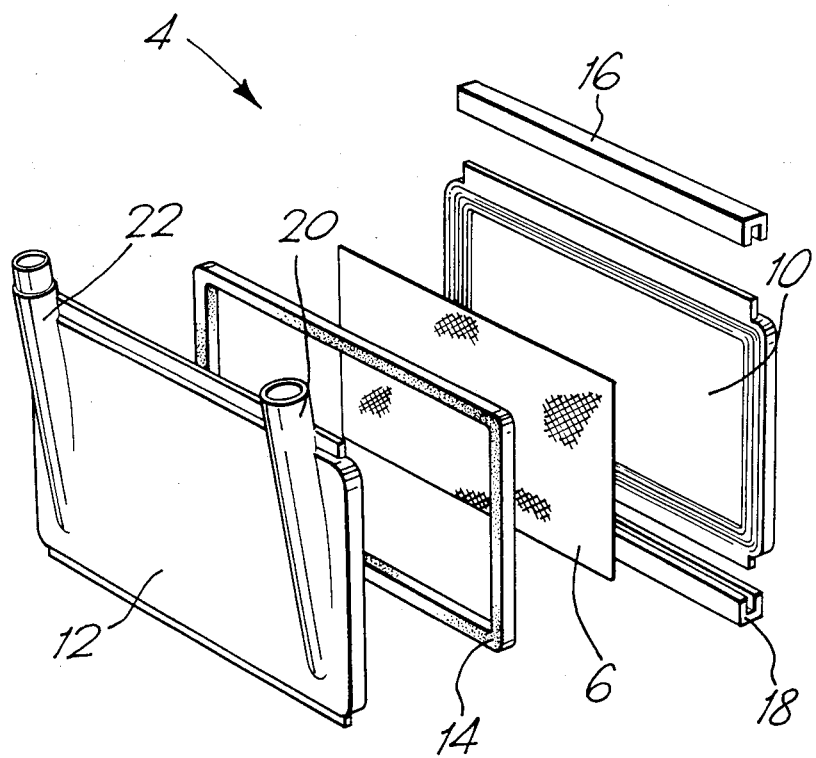
FIG. 3 is an exploded perspective view of the humidifying module of FIG. 2.

Referring also to FIGS. 3, 4 and 5, the humidifying module 4 includes a substantially flat wick 6 accommodated within a humidifying chamber. The wick 6 can be made from an absorbent paper which absorbs water without any significant change in its surface area or from absorbent paper which is provided with slots along its grain to allow for expansion across the grain of the paper. The humidifying chamber is defined by a substantially flat back plate 10 and a front plate 12. Between the plates 10, 12 is a gasket 14 and clamps 16, 18 ensure that the plates 10, 12 are secured together in a gas-tight manner. The front plate 12 incorporates an inlet 20 for dry gas and spaced therefrom an outlet 22 for humidified gas. A further inlet 24 shown most clearly in FIG. 5 permits the passage into the chamber of water.

In use, the humidifying module 4 is releasable attached to the heating unit 2 by means of a locking plate 26 which incorporates sensors 28 to sense a) when the humidifying module 4 is correctly assembled to the heater unit and b) the level of water in the chamber. When operatively attached to the heating unit 2, the module 4 occupies a plane at an angle to the vertical so that one component of gravity forces the wick 6 on to the plate 10. A further advantage of having the module occupy a plane at an angle to the vertical is that it increases the rate of absorption of the water as compared with when the module is arranged vertically.

When assembled ready for use, a heater element 30 which is substantially the same area as the wick 6 and forms part of the heater unit 2 engages the rear (outer) surface of the back plate 10 and is thereby immediately adjacent the wick 6. In operation, water is fed into the chamber by inlet 24 from a water supply 34 and a control unit 36 until the sensors 28 establish that there is a predetermined level of water in the chamber. Heat is supplied to the water by heating element 30 via back plate 10. Dry gas to be humidified then enters the chamber by inlet 20 and passes along the wick 6. Humidified gas then leaves the chamber via outlet 22 to proceed via a delivery hose 40 to the patient in a manner known in the art.

It will be evident that the chamber has a low internal volume and hence a low compliance enabling it to be used for patience ranging from neonates to adults.

Furthermore, its low thermal mass renders it fast to respond to variations in gas flow and temperature.

A particular advantage of the flat wick is that it has a large effective surface area which increases the efficiency of the humidifying module and hence permits a lower temperature source at the heating element 30.

The humidifying module is available either as a pre-sterile disposable module or an autoclavable reusable module.

I claim:

1. An apparatus for delivering humidified gas to a patient comprising a humidifying module including a reservoir and releasably attached to a heater unit and when so attached occupying a plane at an angle with the vertical, the module including a substantially flat back plate and a front plate spaced therefrom, means for clamping the back plate and the front plate together to define a gas tight humidifying chamber, a substantially flat wick accommodated within the humdifying chamber, the wick being made from material that absorbs water without any significant change in its surface area, an inlet for dry gas and an outlet for humidified gas both formed in the front plate for communication with the interior of the humidifying chamber.

2. An apparatus as claimed in claim 1, in which the humidifying module includes a heater unit having a heater element which is substantially the same area as the flat wick and is immediately ajacent thereto.

* * * * *